United States Patent [19]

Jackson et al.

[11] 4,237,231

[45] Dec. 2, 1980

[54] METHOD OF PURIFYING GLUCOSE ISOMERASE AND A COMPOSITION FOR STORING SAME

[75] Inventors: Denise M. Jackson, Chicago; Yoshihisa Tsuda, Highland Park, both of Ill.

[73] Assignee: UOP Inc., Des Plaines, Ill.

[21] Appl. No.: 93,570

[22] Filed: Nov. 13, 1979

[51] Int. Cl.$^3$ .............................................. C12N 9/92
[52] U.S. Cl. .................................. 435/234; 435/814; 435/816; 435/827; 435/886; 435/890; 435/853
[58] Field of Search ................ 435/234, 233, 814, 816

[56] References Cited

U.S. PATENT DOCUMENTS 4,077,842   3/1978   Cory ..................................... 435/188

OTHER PUBLICATIONS

Palleroni et al., "Mannose Isomerase of *Pseudomonas saccharophila*," Journal of Biological Chemistry, 1956, vol. 218, pp. 535–548.
Yamanaka, "D-Xylose Isomerase," Methods in Enzymology, vol. IX, pp. 588–593 (1966).
Takasaki et al., "Studies on Sugar Isomerizing Enzyme," Agr. Biol. Chem., vol. 33, No. 11, pp. 1527–1534 (1969).

*Primary Examiner*—Lionel M. Shapiro
*Attorney, Agent, or Firm*—James R. Hoatson, Jr.; Raymond H. Nelson; William H. Page, II

[57] ABSTRACT

A process for purifying glucose isomerase comprises the steps of acid treatment and salt fractionation. An enzyme solution is treated with an acid, such as acetic acid, to a pH from about 3.5 to about 5.0. The proteinaceous solids are collected and extracted with a buffer, such as imidazole, whose solution has a pH of about 6 to about 8. The solution is then collected and a salt, such as ammonium sulfate, is dissolved therein from about 40% to about 50% of its saturation point. The proteinaceous solids which form are removed and additional ammonium sulfate is dissolved to attain from about 41% to about 60% of its saturation point, followed by collection of the solids containing purified enzyme. A composition which preserves enzyme activity upon storage of glucose isomerase and which imparts resistance to thermal deactivation of said enzyme comprises an aqueous solution of glycerol, a buffer whose solution is at a pH of about 6 to about 8, divalent cobalt ions and magnesium ions.

13 Claims, No Drawings

METHOD OF PURIFYING GLUCOSE ISOMERASE AND A COMPOSITION FOR STORING SAME

BACKGROUND OF THE INVENTION

It is known that fructose is substantially sweeter than glucose. Because the latter is relatively inexpensive and readily available, it is desirable to have an efficient and economical means of converting glucose to fructose. The alkali isomerization of glucose yields fructose, but the production of undesirable side products and the necessity of removing caustic and other materials from a food ingredient make this route unattractive. A preferred method of isomerization utilizing enzymes has the advantages of specificity of reaction and lesser likelihood of producing undesirable side products which must be removed before the fructose-containing material can be used in foods. The enzymes which effect the conversion of glucose to fructose are called glucose isomerases and are formed from such bacteria belonging, inter alia, to the genus Arthrobacter and the genus Actinoplanes. These enzymes are water soluble, and if they are merely added to aqueous solutions of glucose, recovery of enzyme for reuse is difficult and expensive. Using the enzyme only once also affords a process which is relatively expensive. Consequently, many techniques have been developed for immobilizing the enzyme in such a way that substantial enzymatic activity in isomerizing glucose to fructose is displayed while the enzyme itself remains rigidly attached to some water-insoluble support, thereby permitting reuse of the enzyme over substantial periods of time and for substantial amounts of glucose-containing solutions. One illustration of a method for immobilizing an enzyme is found in Levy and Fusee, U.S. Pat. No. 4,141,857, where a polyamine is adsorbed on a metal oxide such as alumina, the resulting composite is treated with an excess of bifunctional reagent, such as glutaraldehyde, so as to crosslink the amine, thereby entrapping the resulting polymer in the pores of the metal oxide, and thereafter contacting the mass with an enzyme to form covalent bonds between the pendant aldehyde groups and a amino groups on the enzyme. It is highly desirable that the material used in making immobilized enzyme contain the desired enzyme, here glucose isomerase, in as chemically pure a state as possible, both to assure maximum loading on the support, and to assure that the immobilized enzyme product will be homogeneous in the kind of enzyme bound to the support, thereby insuring maximum specificity in the conversion of glucose to fructose.

SUMMARY OF THE INVENTION

Accordingly, a principal object of this invention is to provide a method of purifying glucose isomerase. One embodiment of the invention comprises treating an enzyme solution with acid to pH from about 3.5 to about 5.0 and collecting solids, extracting these solids with a buffer whose solution is at pH 6–8 and collecting the solution, dissolving additional salt to 41–60% of its saturation point and collecting the solids containing purified enzyme. A more specific embodiment comprises application of the process wherein said glucose isomerase is produced during the growth of a microorganism of the genus Actinoplanes on a culture. A still more specific embodiment of our invention utilizes imidazole as the buffer, acetic acid as the acid precipitating agent, and ammonium sulfate as the salt wherein the temperature is maintained from about 0° C. to about 20° C. throughout the process.

Another object of this invention is to provide a composition which imparts storage stability and thermal resistance to deactivation of the enzyme. A specific embodiment comprises an aqueous solution of glycerol containing a buffer whose solution is at a pH of about 6 to about 8 and containing divalent cobalt ions.

Other objects and embodiments will be apparent from the description within.

DESCRIPTION OF THE INVENTION

Enzymes with glucose isomerase activity are produced by many microorganisms, including those of the genus Streptomyces, Lactobacillus, Curtobacterium, and Actinoplanes. Examples of particular species of glucose isomerase producers from the above genera include: *A. missouriensis, A. philippenensis, A. armeniacus, L. pentosus, L. breves, C. citreum, C. luteum, C. helvolum*, etc. The Streptomyces are particularly rich in glucose isomerase producers, and examples of such species include *olivochromogenes, venezuelae, coelicolor, aureus, griseolus*, and *virginiae*. By way of illustration only, *A. missouriensis* may be cultured on a medium containing a suitable carbon source and other appropriate nutrients for a time sufficient to give maximum, or near maximum, glucose isomerase activity. The whole cells containing the enzymes are collected by suitable means, such as filtration, washed, then freeze dried and resuspended in a buffer at a pH of about 6 to about 8. In a preferred embodiment the buffer is selected from the group consisting of imidazole, phosphate, and tris(hydroxymethylamino)methane, and any combination thereof. It is contemplated within the scope of this invention that other buffers may be used, but not necessarily with equivalent results. In addition, if so desired, the buffered solution may also contain divalent cobalt ions in the range from about $10^{-4}$ to about $10^{-2}$ molar, and magnesium ions in the range from about $10^{-3}$ to about $10^{-1}$ molar.

To release the enzyme from the cells the cell walls must be ruptured. Examples of suitable means include chemical rupture as by digestion with a lysozyme enzyme preparation, or physical rupture as by rending the walls with sound waves (sonication) or mechanical grinding. In one embodiment the enzyme may be released by sonication at a temperature between about 0° and about 15° C. The cell debris which is formed is then removed by any means known to those skilled in art, as for example, by centrifugation, to afford a solution containing glucose isomerase. In order to denature undesired proteinaceous material, this solution may be heated to a temperature from about 40° C. to about 80° C. for an interval from about 5 to about 60 minutes. However, such heat treatment may be omitted, although not necessarily with equivalent results. In one embodiment the solution is heated from about 55° C. to about 65° C. for a period from about 10 to about 30 minutes. At the completion of the heat denaturation cycle the mixture may be cooled rapidly to about 0° C. to about 20° C., the precipitated material is then removed by suitable means, centrifugation for example, and discarded.

The subsequent operations in the present process are performed at temperatures in the range from about 0° C. to about 20° C., and preferably in a range of from about 0° C. to about 5° C. The cooled solution is acidified until the pH is in the range from about 3.5 to about 5.0. In the case of glucose isomerase from *A. missouriensis* the preferred pH range is from about 3.6 to about 4.4. Example of acids which may be used include inorganic acids, such as hydrochloric, organic carboxylic acids, such as citric, acetic, propionic, butyric and the like, and organic sulfonic acids such as benzenesulfonic acid, toluene sulfonic acid, methanesulfonic acid, and the like. It is to be understood that these examples are not limitations of the invention, and others may be used, but not necessarily with equivalent results. In a preferred embodiment of the invention the acid employed is acetic acid. The solids which form upon acidification are then collected by suitable means, such as centrifugation, and subsequently resuspended in a buffer, preferably selected from the aforementioned group, at a pH from about 6 to 8. This buffer may also contain divalent cobalt ions, or magnesium ions, or any combination thereof, in their aforementioned molarity ranges. Such resuspension is equivalent to extraction of glucose isomerase because not all of the solids obtained upon acidification are soluble in said buffer, and these solids are removed by suitable means and discarded.

The enzyme in solution is now further purified by salt fractionation. A salt is added to the cooled solution in an amount corresponding to about 40% to about 50% of its saturation point (that is, the total amount of salt which can be dissolved in the solution). In a preferred embodiment, the salt must have a solubility such that about 4 molar solutions at 0° C. can be prepared, but is otherwise without limitation. Examples of such salts include ammonium sulfate, ammonium acid sulfate, sodium chloride, potassium acetate, potassium carbonate, and potassium chloride. In another preferred embodiment the salt is an alkali metal or alkaline earth metal sulfate, such as $Li_2SO_4$, $Na_2SO_4$, $K_2SO_4$, $Rb_2SO_4$, $Cs_2SO_4$, and $MgSO_4$. After allowing the solids to precipitate for a period from about 5 to about 60 minutes, preferably for a period from about 10 to 20 minutes, the solids are removed by suitable means and discarded. At this point an additional amount of the salt is dissolved such that the total amount in solution corresponds from about 41 to about 60% of its saturation point, preferably from about 50 to about 60% of its saturation point, thereby causing precipitation of glucose isomerase. After a period of from about 5 to about 60 minutes, but preferably from about 10 to about 30 minutes, the precipitate of purified glucose isomerase is collected by suitable means, such as centrifugation.

Salts can be removed from the purified enzyme by any means, such as, for example, by dialysis or gel permeation chromatography. The solid which is collected as described above is redissolved in a buffer, preferably selected from the aforementioned group, at a pH from about 6 to about 8, which buffered solution may also contain divalent cobalt and/or magnesium ions in their respective aforementioned ranges. This enzyme solution is dialyzed overnight against the same solvent used to dissolve the enzyme, i.e., a solution of the same buffer containing divalent cobalt and/or magnesium ions at the same concentration used for solution of the enzyme. The process of the present invention thus affords an enzyme with up to about 9-fold purification, by which is meant that the specific activity, expressed in units of activity per milligram of protein, is about 9-fold greater for the final enzyme preparation that it was for the initial enzyme preparation. In addition, total recoveries of glucose isomerase range up to about 85%, by which is meant that the total activity of the final enzyme preparation is 85% of that of the initial enzyme preparation.

A surprising discovery is that solutions of certain compositions enhance the time periods during which glucose isomerase can be stored without losing substantial activity, and that these same solutions impart enhanced resistance to thermal deactivation of said glucose isomerase. These solutions contain glycerol in amounts ranging from about 5% to about 60% on a volume-volume basis, imidzaole as a buffer at a pH of about 6 to about 8, divalent cobalt ion in a concentration of about $10^{-4}$ to about $10^{-2}$ molar, and magnesium ion in a concentration of about $10^{-3}$ to about $10^{-1}$ molar. The ability of the aforementioned solution to impart these desirable properties to the enzyme will be shown in greater detail in the examples which are appended to the specification.

The following examples illustrate the process described in this invention and the composition of matter of the storage solution described in the invention. These examples are merely illustrative and it is to be understood that the present invention is not limited thereto.

EXAMPLE 1

Actinoplanes missouriensis (NRRL-3342) was cultured aerobically at 29° C. in a fermentor using the following medium (per 10 liters):

| | |
|---|---|
| 200 g. | Casein Hydrolysate |
| 100 g. | Yeast Autolysate |
| 50 g. | NaCl |
| 5 g. | L-Cystine |
| 5 g. | $Na_2SO_3$ |
| 30 ml. | 1 M $MgSO_4$ $7H_2O$ |
| 500 ml. | 1 M Potassium phosphate buffer, pH 7.0 |
| 50 g./500 ml. | Galactose, autoclaved separately |

Cells were harvested by filtration after an inoculum of 0.05 volume of fresh mature cultures. The cell paste was washed once with 0.05 M phosphate buffer, pH 7.0, containing 9 g. NaCl per liter to give a yield of cells of about 60 g. (dry weight) per 10 liters having an enzyme activity of about 1200 units/gram dry cells.

Enzyme activity was assayed as follows. Glucose isomerase catalyzes formation of an equilibrium mixture of glucose and fructose. The method of assay utilized in these examples is to measure the initial rate of glucose formation from fructose at 60° C. as opposed to the usual assay method which measures the initial rate of fructose formation from glucose. A 1.0 ml. portion of appropriately diluted enzyme or enzyme-containing cells was mixed with an assay solution which contained fructose, 2.5M tris(hydroxymethylamino)methane hydrochloride buffer, $2 \times 10^{-2}$M, at pH 7.5, magnesium sulfate, $5 \times 10^{-3}$M, and cobaltous chloride, $5 \times 10^{-4}$M. After incubation at 60° C. for 30-60 minutes the reaction was terminated by addition of 1 ml. of 0.1N hydrochloric acid, and the glucose formed was measured with a glucose analyzer. One unit of glucose isomerase activity corresponds to formation of 1 micromole glucose per minute. Specific activity corresponds to micromoles of glucose formed per minute per milligram of protein used.

The freeze-dried cells were suspended in 50 mM imidazole buffer, pH 7.0, containing $10^{-2}$M $MgSO_4$ and $10^{-3}$M CoCl$_2$, to a concentration of 5% (w/v) and subjected to sonic disintegration at about 8° C. for 12 minutes. All subsequent operations were carried out at 0°–4° C. except heat treatment of the enzyme. The sonically disintegrated mixture was centrifuged at 12,000 rpm for 10 minutes and the cell debris discarded. The supernatant (780 ml.) was heated at 60° C. for 20 minutes, then cooled quickly in an ice bath. Precipitated protein was removed by centrifugation (12,000 rpm for 10 min.) and discarded. The supernatant (675 ml.) from heat treatment was further purified by acid precipitation. To the clear supernatant solution, a 2N acetic acid solution was added until the pH of the enzyme solution reached pH 4.0. Precipitate was collected after several minutes by centrifugation (12,000 rpm). This pellet of protein was resuspended with a tissue homogenizer in about 170 ml. of 0.2M of an imidazole buffer at pH 7.0 containing $10^{-2}$M MgSO$_4$ and $10^{-3}$M CoCl$_2$. Insoluble precipitate was then removed by centrifugation.

Solid ammonium sulfate was added to the clear supernatant to 45% saturation. After 15 minutes, the mixture was centrifuged (20 min. at 16,000 rpm) and precipitate was discarded. The resulting supernatant received additional ammonium sulfate to 55% saturation. After 15 minutes, the precipitate was collected by centrifugation and dissolved in about 50 ml. of 0.05M of an imidazole buffer, pH 7.0, containing $10^{-2}$M MgSO$_4$ and $10^{-3}$M CoCl$_2$. The solution was dialyzed overnight against the same buffer. The following table shows that about a 9-fold purification with over 80% recovery from crude extract was obtained.

TABLE I

| Fraction | Summary of the Purification of Glucose Isomerase | | | | | | |
|---|---|---|---|---|---|---|---|
| | Volume (ml) | Activity Units/ml | Total Units | Protein mg/ml | Specific Activity (units/mg) | Yield (%) | Purification |
| Crude Extract | 780 | 51.6 | 40,248 | 28.3 | 1.82 | (100) | |
| Heat Treatment | 675 | 51.6 | 34,830 | 13.9 | 3.71 | 86.5% | 2.0 |
| Acid Precipitation | 192 | 135 | 25,920 | 15.8 | 8.54 | 64.4% | 4.7 |
| 45–55% (NH$_4$)$_2$SO$_4$ | 63 | 528 | 33,264 | 33 | 16 | 82.6% | 8.8 |

The data of Table I clearly shows that initially the enzyme preparation showed an activity of 1.82 units/mg protein, whereas after the application of the process of this invention the enzyme preparation showed an activity of 16 units/mg protein, corresponding to an increase of about 9-fold. There was initially present 40,248 units of activity, and after the application of the process of this invention there was present 33,264 units of activity, corresponding to recovery of over 80% glucose isomerase activity.

The glucose isomerase so purified shows unexpected stability in a solution of an imidazole buffer, at neutral pH, containing glycerol and divalent cobalt ions. When stored in an aqueous solution containing 25% glycerol on a volume-volume basis, imidazole buffer at pH 7.0, and $10^{-3}$ molar CoCl$_2$, the glucose isomerase shows no detectable decrease in activity after a month at either 4° C. or −40° C. In stark contrast, the purified glucose isomerase showed loss of more than 50% of its activity when stored for 2 months at −40° C. in 0.1M phosphate buffer. Addition of glycerol at a concentration of 25% to 50% on a volume-volume basis, to the phosphate buffer did not have appreciable beneficial effects. That divalent cobalt ions impart thermal resistance to deactivation of purified glucose isomerase is shown dramatically by the following observation. Purified enzyme dissolved in an imidazole buffer at pH 7.0 containing $10^{-3}$ molar CoCl$_2$ showed no loss of activity when heated to 60° C. for 60 minutes. When the same enzyme was dissolved in the same buffer in the absence of divalent cobalt ions, there was more than a 30% loss of activity when heated to 60° C. for only 20 minutes.

EXAMPLES 2–5

These examples show the pH range over which acidification is effective to purify glucose isomerase from A. missouriensis by precipitation. In all examples 30 ml. of a heat-treated enzyme solution were used. To each was added a sufficient amount of 1 N acetic acid to adjust the pH in increments of 0.5 unit from a pH of 5.0 to 3.5. The resulting precipitate was separated from the supernatant solution and dissolved in a phosphate buffer. Total enzyme activity was measured for both the supernatant and the solution of the formed precipitate with the results shown in Table II.

TABLE II

| | | Total Units of Activity | |
|---|---|---|---|
| Example | pH | Supernatant | Precipitate |
| 2 | 5.0 | 1922 | 0 |
| 3 | 4.5 | 1972 | 0 |
| 4 | 4.0 | 0 | 1366 |
| 5 | 3.5 | 0 | 0 |

These data show that this enzyme is not precipitated at pH 4.5 and above, and that it is completely deactivated at pH 3.5 and below. Glucose isomerase from other microorganisms may have similarly narrow ranges of pH within which enzyme precipitation is effectively induced.

EXAMPLES 6–10

Experiments to determine the optimum salt concentration for fractionation of glucose isomerase from A. missouriensis were performed in the following manner. To aliquot portions of equal volume of acid-precipitated enzyme in a buffer there was added ammonium sulfate in concentrations ranging from 35–55% of its saturation point. Solids were separated from the supernatant solution and dissolved in about 3 ml. of phosphate buffer. One ml. portions each of the supernatant and the solution from precipitated solids were assayed for glucose isomerase activity. Results are shown in Table III.

TABLE III

| Example | Saturation Level of (NH$_4$)$_2$SO$_4$ | Activity per ml Supernatant | Activity per ml Precipitate |
|---|---|---|---|
| 6 | 35% | 82.9 | 0 |
| 7 | 40% | 86.8 | 0 |
| 8 | 45% | 70.4 | 0 |
| 9 | 50% | 42.7 | 38.9 |
| 10 | 55% | 10.0 | 74.8 |

The data of Table III clearly show that when added at levels up to 45% of its saturation point ammonium sulfate causes selective precipitation of glucose isomerase-inactive proteins. After these are removed, further addition of ammonium sulfate causes selective precipitation of glucose isomerase-active proteins, thereby effecting a purification of glucose isomerase.

We claim as our invention:

1. A process for purifying the enzyme glucose isomerase which comprises:
    (a) treating an enzyme solution with acid to a pH from about 3.5 to about 5.0 and collecting the proteinaceous solids;
    (b) extracting the proteinaceous solids with a buffer whose solution is at pH 6–8 and collecting the solution;
    (c) dissolving therein sufficient salt to attain from about 40% to about 50% of its saturation point and collecting the solution; and
    (d) dissolving additional salt in an amount sufficient to attain from about 41% to about 60% of its saturation point and collecting solids containing purified enzyme.

2. The process of claim 1 wherein said glucose isomerase is produced during the growth of a microorganism selected from the group consisting of the genera Actinoplanes, Streptomyces, and Lactobacillus on a culture medium.

3. The process of claim 2 wherein said microorganisms of the genus Actinoplanes are species selected from the group consisting of missouriensis, philippinensis, and armeniacus.

4. The process of claim 2 wherein said microorganisms of the genus Streptomyces are species selected from the group consisting of olivochromogenes, venezuelae, coelicolor, aureus, griseolus, and virginae.

5. The process of claim 1 wherein the temperature is maintained from about 0° C. to about 20° C.

6. The process of claim 1 wherein the buffer is selected from the group consisting of imidazole, phosphate, tris(hydroxymethylamino)methane and combinations thereof.

7. The process of claim 6 wherein the buffer is imidazole.

8. The process of claim 1 wherein the buffered solution contains ions selected from the group consisting of divalent cobalt, at a concentration from about $10^{-4}$ to about $10^{-2}$ molar, magnesium, at a concentration from about $10^{-3}$ to about $10^{-1}$ molar, and combinations thereof.

9. The process of claim 1 wherein the acid is selected from the group consisting of hydrochloric, citric, acetic, propionic, butyric acid, organic sulfonic acids and combinations thereof.

10. The process of claim 9 wherein the acid is acetic acid.

11. The process of claim 1 wherein the salt used in step (d) has a minimum solubility at about 0° C. in water equivalent to that of about a 4 molar solution.

12. The process of claim 11 wherein the salt used in step (d) is ammonium sulfate.

13. The process of claim 1 wherein the salt used in step (d) is selected from the group consisting of alkali metal sulfates and alkaline earth metal sulfates.

* * * * *